United States Patent
Wada et al.

(10) Patent No.: US 8,234,930 B2
(45) Date of Patent: Aug. 7, 2012

(54) METHOD OF DETERMINING FATIGUE OF PRESSURE-RESISTANT COMPONENT FOR HIGH-PRESSURE HYDROGEN

(75) Inventors: Yoru Wada, Muroran (JP); Ryoji Ishigaki, Muroran (JP); Yasuhiko Tanaka, Tokyo (JP)

(73) Assignee: The Japan Steel Works, Ltd., Tokyo (JP)

( * ) Notice: Subject to any disclaimer, the term of this patent is extended or adjusted under 35 U.S.C. 154(b) by 215 days.

(21) Appl. No.: 12/669,798

(22) PCT Filed: Jul. 18, 2008

(86) PCT No.: PCT/JP2008/063064
§ 371 (c)(1),
(2), (4) Date: Jun. 28, 2010

(87) PCT Pub. No.: WO2009/014104
PCT Pub. Date: Jan. 29, 2009

(65) Prior Publication Data
US 2011/0167921 A1   Jul. 14, 2011

(30) Foreign Application Priority Data
Jul. 20, 2007   (JP) ................. 2007-190100

(51) Int. Cl.
*G01N 3/32* (2006.01)
*G01N 19/08* (2006.01)

(52) U.S. Cl. ................. 73/807; 73/810; 73/799
(58) Field of Classification Search ......... 73/799, 73/807, 810
See application file for complete search history.

(56) References Cited

PUBLICATIONS

"Evaluation of Hydrogen Embrittlement Susceptibility of 2.25Cr-1Mo Steel for Pressure Vessel after Long-Term Service", The Japan Pressure Vessel Research Council, 2001, pp. 2.
Imade, M., et al., "Hydrogen Embrittlement of SCM440 Steel in High-pressure Hydrogen at Room Temperature", Nihon Kinzoku Gakkai Shi, Feb. 20, 2005, pp. 190-193, vol. 69, No. 2.
Murakami, Y., "Difficult Problem in Hydrogen Utilization Technologies/How Hydrogen Lessens Strength of Materials", Kiho Enerugi Sogo Kogaku, Jul. 20, 2005, pp. 22-29, vol. 28, No. 2.
Lewis, B. A., et al., "The effect of surface finish on the deformation characteristics of 1015 steel at 25° C.", Met Hydrogen Syst, 1982, pp. 347-353.
"Standards of the High Pressure Gas Safety Institute of Japan", Chokoatsu Gasu Setsubi Ni Kansuru Kijun KHK S 0220, 2004, pp. 38.
"2004 ASME Boiler and Pressure Vessel Code", American Society of Mechanical Engineers, 2006, pp. 39, Section VIII, Division 3, Part KD300.
"Data for Fatigue Strength Design (II)", Hyomen Jotai, Hyomen Shori, 1982, pp. 3-4, revised 2nd ed., The Japan Society of Mechanical Engineers.

*Primary Examiner* — Lisa Caputo
*Assistant Examiner* — Jonathan Dunlap
(74) *Attorney, Agent, or Firm* — Sughrue Mion, PLLC (57) ABSTRACT

A method of determining fatigue of a pressure-resistant component for high-pressure hydrogen made of a ferritic steel and provided in a high-pressure hydrogen gas environment is provided wherein when the material of the ferritic steel in the air has an ultimate tensile strength Su in the range of 958-1,144 MPa and the hydrogen gas environment has a pressure in a range to 45 MPa, then a fatigue strength in a gaseous hydrogen $S_H$ (MPa) for the pressure-resistant component provided in the high-pressure hydrogen gas environment is obtained by using equation (1): $S_H$ (MPa)=2,577−1.8925×Su (MPa). The influence of a high-pressure hydrogen gas environment on the pressure-resistant component for high-pressure hydrogen is determined based on the fatigue strength obtained by using the equation (1).

7 Claims, 5 Drawing Sheets

METHOD OF DETERMINING FATIGUE OF PRESSURE-RESISTANT COMPONENT FOR HIGH-PRESSURE HYDROGEN

TECHNICAL FIELD

The present invention relates to a method of determining fatigue of a pressure-resistant component for high-pressure hydrogen, for use in high-pressure hydrogen devices in, e.g., pressure accumulators and compressors for hydrogen gas stations.

BACKGROUND ART

High-pressure hydrogen vessels and the like which are exposed to a hydrogen gas environment have a problem concerning embrittlement thereof caused by contact with hydrogen. In non-patent literature 1, one class of hydrogen damages is defined as HEE (hydrogen environment embrittlement). Reports on investigations concerning hydrogen embrittlement include non-patent literature 2, in which samples that had been regulated through a heat treatment so as to differ in strength were subjected to a tensile test in a high-pressure hydrogen atmosphere in order to elucidate tensile properties of materials placed in high-pressure hydrogen, and an influence of hydrogen pressure and strain rate is investigated. In non-patent literature 3, a material of a pressure accumulator or hydrogen compressor (chromium-molybdenum steel (SCM435)) was subjected to a fatigue test after hydrogen had been infiltrated thereinto beforehand.

It has been reported therein that even when an amount of internal hydrogen was slight, a decrease in fatigue strength and a decrease in fatigue life were observed. Furthermore, in non-patent literature 4, there is a report that a titled material which had undergone various kinds of surface finishing polishing with alumina varying from 240 grit to 0.05 μm) was subjected to a burst test in hydrogen and oxygen and, as a result, a leakage-induced failure was accelerated in hydrogen as the surface finishing became rougher, while no surface effect was observed in oxygen.

Non-patent literature 5 shows standards of The High Pressure Gas Safety Institute of Japan, and it is prescribed that a stress concentration factor due to surface roughness should be taken into account in a procedure for fatigue analysis. Non-patent literature 6 describes a method according to ASME for taking account of the stress concentration factor due to the surface roughness of a pressure vessel in a procedure for fatigue analysis Non-patent literature 7 shows values of residual stress resulting from various kinds of processing.

Incidentally, a pressure accumulator of a hydrogen gas station, for example, is supposed to undergo repeated pressure charging about 100 times per day, or about 36,500 times per year. It is therefore necessary to take account of fatigue when a high-pressure hydrogen device is designed.

In a related method for determining the fatigue of high-pressure gas facilities without taking account of a hydrogen gas environment, it is required, in the case of using a high service pressure, to multiply a stress amplitude due to fatigue by stress concentration factor due to surface roughness when a fatigue design is made (see, for example, non-patent literature 5, page 38 and non-patent literature 6, KD page 322).

Non-Patent literature 1: "Evaluation of Hydrogen Embrittlement Susceptibility of 2.25Cr-1Mo Steel for Pressure Vessel after Long-Term Service", The Japan Pressure Vessel Research Council, 2001, pp. 2.

Non-Patent literature 2: IMADE Masaaki, FUKUYAMA Seiji, ZHANG L, WEN M, YOKOGAWA Kiyoshi (National Institute of Advanced Industrial Science and Technology, Research Institute of Instrumentation Frontier), "Hydrogen Embrittlement of SCM440 Steel in Room-Temperature High-Pressure Hydrogen Atmosphere", Nihon Kinzoku Gakkai Shi, published on Feb. 20, 2005, Vol. 69, No. 2, pp. 190-193, Tracing 7, Table 1, Ref. 18.

Non-Patent literature 3: MURAKAMI Yukitaka (Kyushu University), "Difficult Problem in Hydrogen Utilization Technologies/How Hydrogen Lessens Strength of Materials", Kihō Enerugī Sōgō Kōgaku, published on Jul. 20, 2005, Vol. 28, No. 2, pp. 22-29.

Non-Patent literature 4: LEWIS B A, LOUTHAN JR M R, WAGNER J, SISSON JR R D, McNITT R P, LOUTHAN III M R (Virginia Polytechnic Inst.), "The effect of surface finish on the deformation characteristics of 1015 steel at 25"C", Met Hydrogen Syst, published in 1982, pp. 347-353.

Non-Patent literature 5: "Standards of The High Pressure Gas Safety Institute of Japan", Chōkōtsu Gasu Setsubi Ni Kansuru Kijun KHK S 0220, published in 2004, pp. 38.

Non-Patent literature 6: ASME Boiler And Pressure Vessel Code, Section VIII, Division 3, Part KD300, p. 39.

Non-Patent literature 7: "Data for Fatigue Strength Design (II)", Hyōmen Jōtai, Hyōmen Shori (revised 2nd ed.), The Japan Society of Mechanical Engineers, published in 1982, pp. 3-4.

DISCLOSURE OF THE INVENTION

Problems that the Invention is to Solve

However, in the related art, it is utterly unknown what effect repeated application of pressure of high-pressure hydrogen gas produces on a fatigue cracking and failure at a processed pressure-part surface, and no fatigue determination method for ensuring safety has been established with respect to material selection and pressure-part surface processing methods.

The invention has been achieved under these circumstances. An object of the invention is to provide a method of determining the fatigue of a pressure-resistant component for high-pressure hydrogen, wherein the influence of a high-pressure hydrogen gas environment on fatigue can be estimated and determined from the method of surface finishing used for the pressure part and from the ultimate tensile strength of the material.

The invention makes it possible to determine the influence of HEE (hydrogen environment embrittlement), which is defined as one class of hydrogen damage's in non-patent literature 1, on fatigue and to establish a designing method, etc. According to the invention, whether the fatigue of a high-pressure gas apparatus to be used in a high-pressure hydrogen gas environment is influenced by the high-pressure hydrogen gas environment or not can be determined.

Means for Solving the Problems

The invention provides a method of determining fatigue of a pressure-resistant component for high-pressure hydrogen, and the method is for determining the fatigue of a pressure-resistant component for high-pressure hydrogen made of a ferritic steel and provided in a high-pressure hydrogen gas environment and is characterized in that when a material of the ferritic steel in an air has an ultimate tensile strength in a range of 958-1,144 MPa and the high-pressure hydrogen gas environment has a pressure in a range up to 45 MPa, the method obtains a fatigue stress in a gaseous hydrogen $S_H$ (MPa) for the pressure-resistant component provided in the high-pressure hydrogen gas environment using following equation:

$$SH(MPa) = 2{,}577 - 1.8925 \times Su(MPa) \quad \text{equation (1)}$$

wherein Su represents the ultimate tensile strength of the material of the ferritic steel material in the air.

The method of determining the fatigue of a Pressure-resistant component for high-pressure hydrogen of the invention may be characterized in that the method determines fatigue properties in the high-pressure hydrogen gas environment of the pressure-resistant component for high-pressure hydrogen based on the fatigue strength obtained by using the equation (1).

The method of determining the fatigue of a pressure-resistant component for high-pressure hydrogen of the invention may be characterized in that the method determines an influence of a high-pressure hydrogen gas environment on the pressure-resistant component for high-pressure hydrogen based on the fatigue strength obtained by using the equation (1).

The method of determining the fatigue of a pressure-resistant component for high-pressure hydrogen of the invention may be characterized in that the method obtains an upper limit of a principal stress difference that gives a cyclic stress amplitude to a pressure-part surface of the pressure-resistant component for high-pressure hydrogen from an average stress, which is to be imposed on a pressure-part surface layer of the pressure-resistant component, and into which residual stress has been incorporated and from the stress amplitude which the pressure-part surface undergoes, and that an influence of the high-pressure hydrogen gas environment on the fatigue properties of the pressure-part surface is determined based on a comparison between the upper limit and the fatigue strength obtained by using the equation (1).

The method of determining the fatigue of a pressure-resistant component for high-pressure hydrogen of the invention may be characterized in that the residual stress is a stress caused in the surface layer during processing of the pressure-part surface.

The method of determining the fatigue of a pressure-resistant component for high-pressure hydrogen of the invention may be characterized in that the stress amplitude is obtained by multiplying a stress concentration factor due to a surface roughness of the pressure-part surface by a nominal stress amplitude.

The method of determining the fatigue of a pressure-resistant component for high-pressure hydrogen of the invention may be characterized in that a relationship between each of surface-finishing methods and surface roughness is predetermined, and that the surface roughness to be used for determining the stress amplitude is estimated based on the surface-finishing method applied to the pressure-part surface.

Advantage of the Invention

As explained above, according to the method of determining the fatigue of a pressure-resistant component for high-pressure hydrogen of the invention, the influence of a high-pressure hydrogen gas environment on the fatigue properties of a pressure-resistant component for high-pressure hydrogen which is provided in the high-pressure hydrogen gas environment can be estimated and determined. The high-pressure hydrogen gas apparatus is prevented from suffering the fatigue failure attributable to the influence of the hydrogen gas environment.

The invention hence has the effect of contributing to the early realization of a hydrogen energy society which is safe and gives a sense of relief.

BEST MODE FOR CARRYING OUT THE INVENTION

One embodiment of the invention is explained below.

Figure 1:
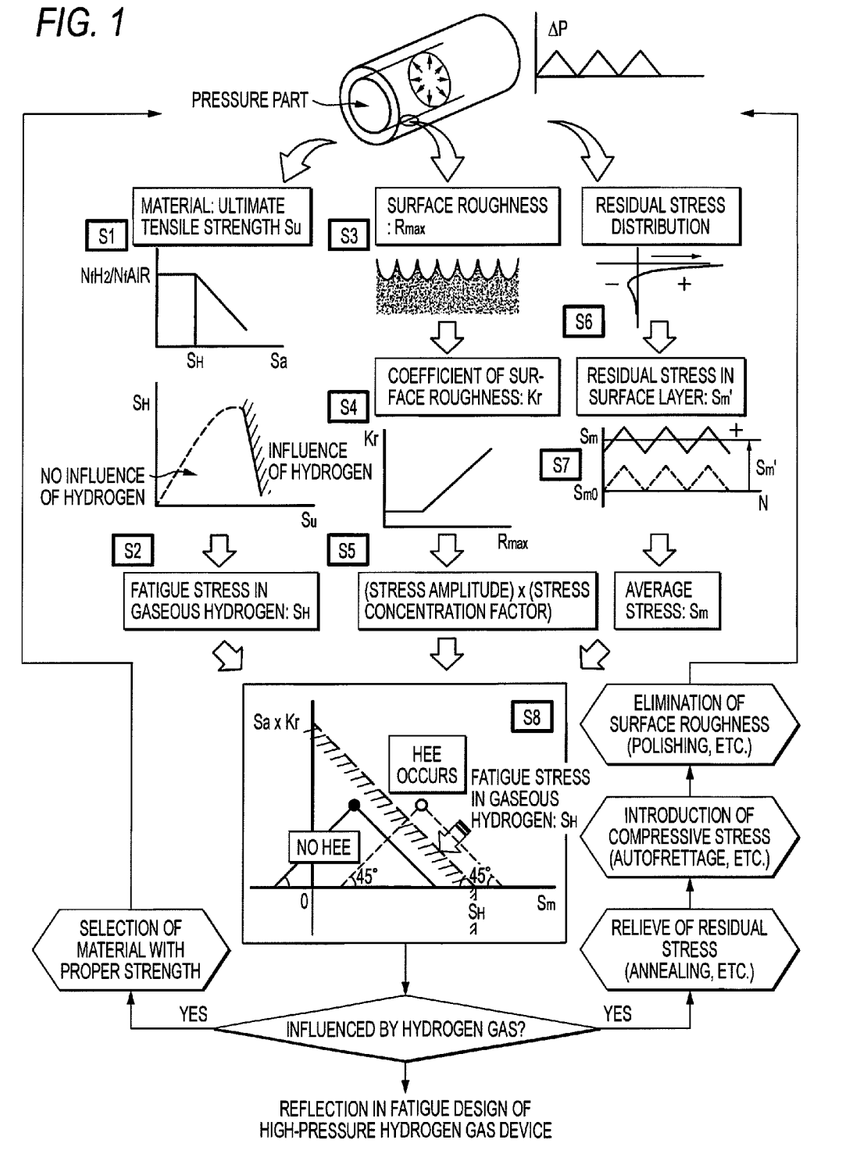
FIG. 1 is a flow diagram illustrating the determination of the influence of a high-pressure hydrogen gas environment in one embodiment of the invention.

FIG. 1 is a flow diagram for estimating and determining the influence of a high-pressure hydrogen gas environment on the fatigue of a pressure part from the method of surface finishing used for the pressure part and from the ultimate tensile strength of the material in this embodiment.

As the material to be provided, a component constituted of a ferritic steel is prepared. The surface of the pressure part is subjected to surface processing and then to suitable finishing.

Although the component to be examined according to the invention is limited to ones constituted of a ferritic steel, the composition itself of the ferritic steel should not be construed as being limited to a specific one. With respect to a definition of ferritic steel, this is a name for distinguishing this steel from nickel-based alloys or austenitic stainless steels. Examples of the ferritic steel include tempered bainitic steels and tempered martensitic steels, such as Cr—Mo steel and Ni—Cr—Mo steel.

Examples of the surface processing include cutting and grinding. Examples of the finishing include grinding finishing, barrel polishing finishing, electropolishing finishing, and buffing finishing. In the invention, the kind of such processing is not limited, and whether the pressure-part surface has undergone such processing or not is also not limited.

A procedure for determination is explained below based on the flow diagram of FIG. 1.

In step S1, the ultimate tensile strength Su which a material has in the air is obtained by actually subjecting the material to a strength test or obtaining a value of the strength from the records or the like for the apparatus. Namely, the ultimate tensile strength of the material may be any value obtained as data, and methods for obtaining a value of the strength are not limited.

In step S2, which succeeds step S1, a fatigue strength in a gaseous hydrogen in a high-pressure hydrogen gas environment is obtained from the in-air ultimate tensile strength of the material obtained in step S1. The procedure therefor is explained below.

Figure 2:
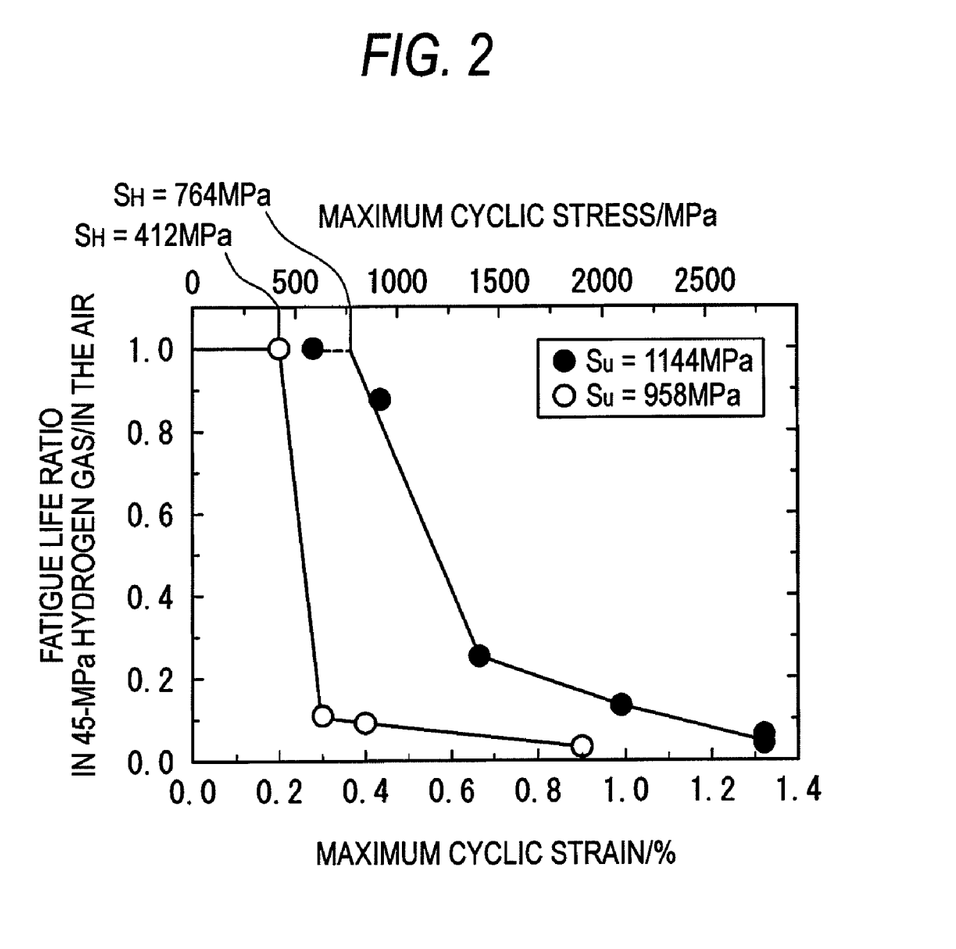
FIG. 2 is a presentation showing the influence of repeated upper-limit stress on the fatigue life ratios (in hydrogen gas/in the air) of commercial ferritic low-alloy steels differing in ultimate tensile strength, in the embodiment.
Figure 3:
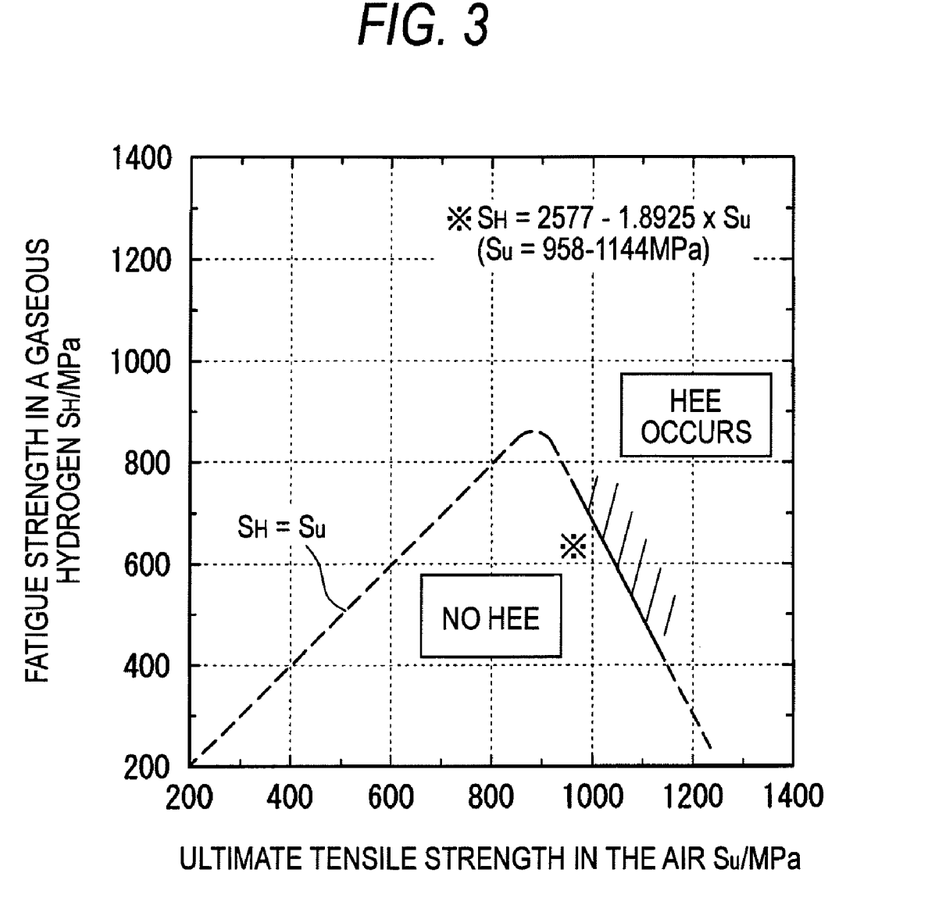
FIG. 3 is a presentation showing the relationship between fatigue strength in a gaseous hydrogen and the ultimate tensile strength of materials as measured in the air, in the embodiment.

FIG. 2 shows the influence of maximum cyclic stress on the fatigue life ratios (in hydrogen gas/in the air) of commercial ferritic low-alloy steels differing in ultimate tensile strength. The fatigue strength in a gaseous hydrogen $S_H$ in a high-pressure hydrogen gas environment is obtained therefrom with respect to each of the materials differing in ultimate tensile strength to show that the fatigue strength in a gaseous hydrogen $S_H$ in a high-pressure hydrogen gas environment depends on the ultimate tensile strength of the material. This dependence on ultimate tensile strength is as shown in FIG. 3. This dependence can be obtained by using the equation (1) when the ultimate tensile strength Su is in the range of 956-1,144 MPa.

On the other hand, in steps S4 and S5, stress concentration due to the surface roughness of the pressure part is taken into account, and a stress concentration factor Kr is obtained from the surface roughness $R_{max}$ by a known method such as that shown in non-patent literature 5 or non-patent literature 6 (diagram showing the relationship between surface roughness and stress concentration factor). The surface roughness $R_{max}$ may be one obtained through a measurement made by a known measuring method, or may be a value estimated from the method of surface finishing. This estimation can be facilitated by setting the relationship between each of surface-finishing methods and $R_{max}$ beforehand. Incidentally, although surface roughness is evaluated in terms of maximum height $R_{max}$ in this embodiment, methods for surface roughness evaluation in the invention should not be construed as being limited thereto. Surface roughness may be evaluated in terms of mean roughness, ten-point average roughness, or the like.

When a stress concentration factor is obtained from the surface roughness, use can be made of a diagram showing the relationship between the surface roughness obtained by any of such evaluation methods and stress concentration factor.

The value of Kr is multiplied by the amplitude of stresses generated in the pressure-part surface by a repeated pressure (nominal stress amplitude) $S_a$.

In step S6, on the other hand, the residual stress Sm' generated in the surface layer by processing is evaluated by X-ray analysis, etc. In the case where X-ray analysis is difficult, the residual stress Sm' may be estimated with reference to, e.g., the values of residual stress resulting from grinding and polishing which are given in, e.g., non-patent literature 7. Namely, methods for obtaining the residual stress are not particularly limited in the invention.

Subsequently, in step S7, the residual stress Sm' generated in the surface layer is added to an average stress Sm0 obtained from fatigue stresses, and the resultant sum is taken as average stress $S_m$.

Figure 4:
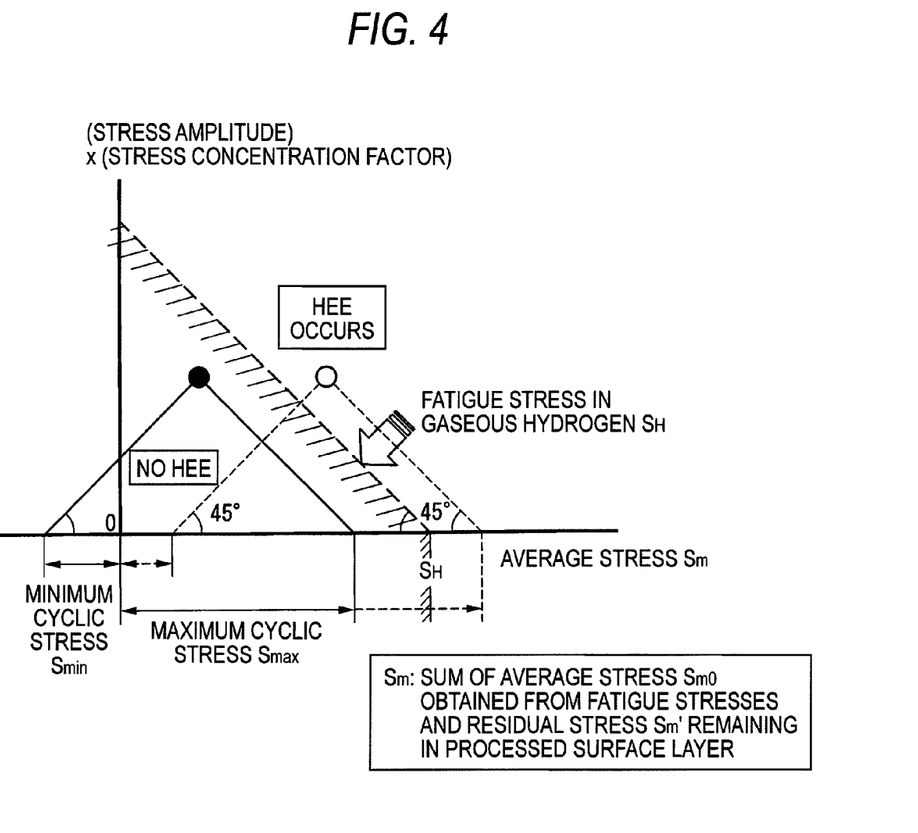
FIG. 4 is a diagrammatic view illustrating a method in which the influence of a hydrogen gas environment is evaluated on a stress amplitude-average stress plan view based on fatigue strength in a gaseous hydrogen $S_H$ as measured in a high-pressure hydrogen gas environment, in the embodiment.

In step S8, on the stress amplitude-average stress plan view shown in FIG. 4, the (stress amplitude $Kr^xS_a$) obtained in step S5 is plotted as ordinate, and the average stress $S_m$ obtained in step S7 is platted as abscissa. When the maximum cyclic stress is outside the region defined by a limit line which passes through $S_H$ and has an inclination of 45° toward the vertical direction for the graph, then it is concluded 10 that a hydrogen gas environment exerts an influence on fatigue (HEE occurs): When the maximum cyclic stress thereof is inside the region, it is concluded that a hydrogen gas environment exerts no influence on fatigue.

The conclusion can be reflected in the fatigue design of a high-pressure hydrogen gas device. In the case where it has been concluded in the determination that a hydrogen gas environment exerts an influence, a design modification for obtaining the conclusion that the environment exerts no influence can be made. For example, a material having a different ultimate tensile strength in the range of 958-1,144 MPa can be selected to make a design for obtaining the conclusion that a hydrogen gas environment exerts no influence. Also in the case where a change in ultimate tensile strength has been made, whether a hydrogen gas environment exerts an influence or not can be determined through steps S1 to S8.

Furthermore, when it has been concluded in the determination that a hydrogen gas environment exerts an influence, a measure for obtaining the conclusion that the environment exerts no influence can be taken. For example, a heat treatment such as annealing for relieving a residual stress resulting from processing can be conducted. Alternatively, a residual stress can be diminished by introducing a compressive stress to a surface layer of the pressure part. Methods for introducing a compressive stress are not particularly limited, and autofrettage or the like can be employed therefor. Other usable measures include to conduct polishing or the like in order to eliminate surface roughness (reduce surface roughness). These measures are effective in reducing average stress and stress amplitude and have the function of enhancing safety concerning fatigue strength.

EXAMPLE 1

As a test material, a commercial low-alloy ferritic steel (SCM440 steel) was used in the form of round-bar test specimen. The ultimate tensile strength of the test pieces was obtained according to the JIS Z 2241, Method of Tensile Test for Metallic Materials. As a result, the ultimate tensile strength thereof was found to be 1,015 MPa.

The surfaces of the round-bar test pieces were ground so as to result in target values of surface roughness $R_{max}$ of 19 μm, 26 μm, and 93 μm. After the grinding, the surface roughness of each test piece was measured. The results thereof are shown in Table 1. These test pieces each were subjected to a fatigue test (test stress $S_a$=500 MPa; stress ratio R=−1) and a fatigue test (test stress $S_a$=400 MPa; stress ratio R=−1) in each of an ultrahigh-purity high-pressure hydrogen gas environment of 45 MPa and the air to evaluate the influence of hydrogen gas on fatigue. The results thereof are shown in Table 1.

Figure 5:
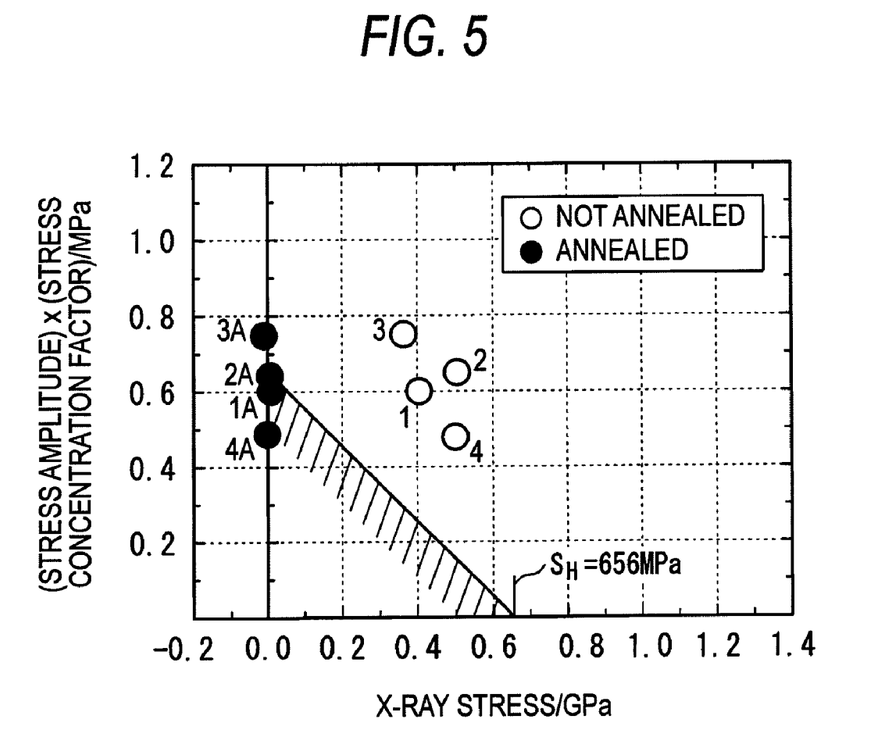
FIG. 5 shows the results of an examination in which whether a high-pressure hydrogen gas environment exerted an influence on fatigue or not was determined, according to the invention, on a stress amplitude-average stress plan view with respect to test pieces of Example according to the invention.

On the other hand, the influence of hydrogen gas on fatigue strength was evaluated through steps S1 to S8 shown in the block diagram of FIG. 1, and the results thereof are shown in Table 2. Furthermore, data on each test piece were plotted on the stress amplitude-average stress (residual stress obtained by X-ray analysis) plan view of FIG. 5 to determine as to whether a high-pressure hydrogen gas environment exerted an influence on fatigue or not. The results thereof are shown in the figure. The results of determination given in Table 2 and FIG. 5 agreed satisfactorily with the tendency of fatigue actually observed in hydrogen gas as shown in Table 1. Whether the fatigue of a pressure part was influenced by a high-pressure hydrogen gas environment or not was able to be precisely determined from the method of finishing the surface of the pressure part and from the ultimate tensile strength of the material.

TABLE 1

| Stress conditions | Sign | Annealing | Target value of $R_{max}$ μm | Found value of $R_{max}$ μm | Number of cycles to failure In the air | Number of cycles to failure In 45 MPaH$_2$ | Influence of high-pressure hydrogen gas |
|---|---|---|---|---|---|---|---|
| $S_a$ = 500 MPa R = −1 | 1 | not annealed | 19.0 | 21.3 | 62,347 | — | influenced |
| | | | | 20.2 | 78,086 | — | |
| | | | | 18.2 | 73,349 | — | |
| | | | | 16.7 | — | 11,354 | |
| | | | | 18.2 | — | 25,785 | |
| | | | | 19.0 | — | 33,987 | |
| | 1A | annealed | 19.0 | 20.1 | 131,552 | — | not influenced |
| | | | | 19.1 | — | 143,679 | |
| | 2 | not annealed | 26.0 | 28.0 | 53,744 | — | influenced |
| | | | | 25.8 | 72,445 | — | |
| | | | | 24.2 | 64,993 | — | |
| | | | | 28.2 | — | 11,598 | |
| | | | | 23.4 | — | 19,870 | |
| | | | | 20.6 | — | 21,933 | |
| | 2A | annealed | 26.0 | 31.3 | 143,679 | — | influenced |
| | | | | 32.8 | — | 103,676 | |
| | 3 | not annealed | 93.0 | 84.7 | 41,866 | — | influenced |
| | | | | 84.7 | 40,686 | — | |
| | | | | 91.9 | — | 5,225 | |
| | | | | 87.7 | — | 11,696 | |
| | | | | 87.5 | — | 13,991 | |
| | 3A | annealed | 93.0 | 94.4 | 98,703 | — | influenced |
| | | | | 90.1 | 93,097 | — | |
| | | | | 93.2 | — | 33,921 | |
| | | | | 93.9 | — | 42,841 | |
| $S_a$ = 400 MPa R = −1 | 4 | not annealed | 15.0 | 15.0 | 294,421 | — | influenced |
| | | | | 15.0 | — | 79,196 | |
| | 4A | annealed | 15.0 | 15.0 | 1000000> | — | not influenced |
| | | | | 15.0 | — | 1000000> | |

TABLE 2

| Step | Sign in Figure | 1 | 1A | 2 | 2A | 3 | 3A | 4 | 4A |
|---|---|---|---|---|---|---|---|---|---|
| — | Target value of surface roughness | $R_{max}$ = 19 μm | | $R_{max}$ = 26 μm | | $R_{max}$ = 93 μm | | $R_{max}$ = 15 μm | |
| — | Heat treatment conditions | not annealed | annealed | not annealed | annealed | not annealed | annealed | not annealed | annealed |
| S1-S2 | Ultimate tensile strength in the air Su (MPa) | | | | | 1015 | | | |
| S3 | Fatigue strength in a gaseous hydrogen $S_H$ (MPa) | | | | | 656 | | | |
| S4 | Kr | 1.23 | | 1.21 | | 1.44 | | 1.20 | |
| S5 | Nominal stress amplitude $S_a$ (MPa) | 500 | | 500 | | 500 | | 400 | |
| | Stress amplitude Kr × $S_a$ (MPa) | 615 | | 635 | | 720 | | 480 | |
| S6 | X-ray stress Sm' (MPa) | 408 | 11 | 506 | 8 | 366 | −13 | 500 | 0 |
| S8 | Maximum cyclic stress Smax Smax = Sm' + Kr × Sa ($S_{m0}$ = 0) | 1023 | 626 | 1141 | 643 | 1086 | 707 | 980 | 480 |
| | Smax > $S_x$ Determination | yes influenced | no not influenced | yes influenced | no not influenced | yes influenced | yes influenced | yes influenced | yes not influenced |

While the invention has been described in detail and with reference to specific embodiments thereof, it will be apparent to one skilled in the art that various changes and modifications can be made therein without departing from the spirit and scope thereof.

This application is based on a Japanese patent application filed on Jul. 20, 2007 (application No. 2007-190100), the contents thereof being herein incorporated by reference.

INDUSTRIAL APPLICABILITY

As explained above, according to the method of the invention for determining the fatigue of a pressure-resistant component for high-pressure hydrogen made of a ferritic steel and provided in a high-pressure hydrogen gas environment, when the material of the ferritic steel in the air has an ultimate tensile strength Su in the range of 956-1,144 MPa and the hydrogen gas environment has a pressure in a range to 45 MPa, then a fatigue strength in a gaseous hydrogen SH (MPa) for the pressure-resistant component provided in the high-pressure hydrogen gas environment is obtained by using following equation.

$$S_H(\text{MPa})=2{,}577-1.5925\times Su(\text{MPa}) \qquad \text{equation (1)}$$

Because of this, the influence of a high-pressure hydrogen gas environment on the fatigue properties of a pressure-resistant component for high-pressure hydrogen which is provided in the high-pressure hydrogen gas environment can be estimated and determined. The high-pressure hydrogen gas apparatus is prevented from suffering the fatigue failure attributable to the influence of the hydrogen gas environment. The invention hence has the effect of contributing to the early realization of a hydrogen energy society which is safe and gives a sense of relief. The method of the invention is useful in the field of the determination of the fatigue of pressure-resistant components for high-pressure hydrogen for use in, e.g., pressure accumulators, compressors, or the like for hydrogen gas stations.

The invention claimed is:

1. A method of determining fatigue of a pressure-resistant component for high-pressure hydrogen made of a ferritic steel and provided in a high-pressure hydrogen gas environment,
    wherein, when a material of the ferritic steel in an air has an ultimate tensile strength in a range of 958-1,144 MPa and the high-pressure hydrogen gas environment has a pressure in a range up to 45 MPa, the method obtains a fatigue strength in a gaseous hydrogen $S_H$ (MPa) for the pressure-resistant component provided in the high-pressure hydrogen gas environment using following equation:

$$S_H(\text{MPa})=2{,}577-1.8925\times Su(\text{MPa}) \qquad \text{equation (1)}$$

wherein Su represents the ultimate tensile strength of the material of the ferritic steel in the air.

2. The method of determining fatigue of a pressure-resistant component for high-pressure hydrogen according to claim 1,
    wherein the method determines fatigue properties in the high-pressure hydrogen gas environment of the pressure-resistant component for high-pressure hydrogen based on the fatigue strength obtained by using the equation (1).

3. The method of determining fatigue of a pressure-resistant component for high-pressure hydrogen according to claim 1,
    wherein the method determines an influence of the high-pressure hydrogen gas environment on the pressure-resistant component for high-pressure hydrogen based on the fatigue strength obtained by using the equation (1).

4. The method of determining fatigue of a pressure-resistant component for high-pressure hydrogen according to claim 1,
    wherein the method obtains an upper limit in cycling of a principal stress difference that gives a stress amplitude to a pressure-part surface of the pressure-resistant component for high-pressure hydrogen from an average stress, which is to be imposed on a pressure-part surface layer of the pressure-resistant component and into which residual stress has been incorporated, and from the stress amplitude which the pressure-part surface undergoes, and
    wherein the method determines an influence of the high-pressure hydrogen gas environment on the fatigue properties of the pressure-part surface based on a comparison between the upper limit and the fatigue strength obtained by using the equation (1).

5. The method of determining fatigue of a pressure-resistant component for high-pressure hydrogen according to claim 4,
    wherein the residual stress is a stress caused in the surface layer during processing of the pressure-part surface.

6. The method of determining fatigue of a pressure-resistant component for high-pressure hydrogen according to claim 4,
    wherein the stress amplitude is obtained by multiplying a stress concentration factor due to a surface roughness of the pressure-part surface by a nominal stress amplitude.

7. The method of determining fatigue of a pressure-resistant component for high-pressure hydrogen according to claim 6,
    wherein a relationship between each of surface-finishing methods and surface roughness is predetermined, and
    wherein the surface roughness to be used for determining the stress amplitude is estimated based on the surface-finishing method applied to the pressure-part surface.

* * * * *